(12) United States Patent
Yumoto et al.

(10) Patent No.: US 9,861,297 B2
(45) Date of Patent: Jan. 9, 2018

(54) GAS ANALYSIS DEVICE AND GAS ANALYSIS METHOD

(71) Applicant: RIKEN, Saitama (JP)

(72) Inventors: Masaki Yumoto, Ibaraki (JP); Koji Miyazaki, Tokyo (JP); Satoshi Wada, Saitama (JP); Takayo Ogawa, Saitama (JP); Shinichi Imai, Tokyo (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 15/063,432

(22) PCT Filed: Sep. 8, 2014

(86) PCT No.: PCT/JP2014/004597
§ 371 (c)(1),
(2) Date: Jun. 3, 2016

(87) PCT Pub. No.: WO2015/033582
PCT Pub. Date: Mar. 12, 2015

(65) Prior Publication Data
US 2016/0331270 A1    Nov. 17, 2016

(30) Foreign Application Priority Data

Sep. 9, 2013   (JP) .................................. 2013-185804

(51) Int. Cl.
*A61B 5/08*   (2006.01)
*G01N 21/3504*   (2014.01)
(Continued)

(52) U.S. Cl.
CPC ............ *A61B 5/082* (2013.01); *A61B 5/0075* (2013.01); *A61B 5/097* (2013.01); *A61B 5/441* (2013.01);
(Continued)

(58) Field of Classification Search
CPC ....................................................... A61B 5/082
See application file for complete search history.

(56) References Cited

U.S. PATENT DOCUMENTS

| 6,229,828 B1 * | 5/2001 | Sanders | ............... G02F 1/3534 |
| | | | 359/326 |
| 6,545,278 B1 | 4/2003 | Mottier et al. | |

(Continued)

FOREIGN PATENT DOCUMENTS

| JP | 2006-300760 A | 11/2006 |
| JP | 2009-222527 A | 10/2009 |

OTHER PUBLICATIONS

International Search Report for International Application No. PCT/JP2014/004597, issued by the Japan Patent Office dated Oct. 21, 2014.

(Continued)

*Primary Examiner* — David Porta
*Assistant Examiner* — Hugh H Maupin

(57) ABSTRACT

To provide a gas analysis device comprising: a cell; a light source; and a detector, wherein two or more types of gaseous components contained in the gas are measurement targets, a mid-infrared light with a wavelength that is caused to match the absorption spectrum of the measurement target gaseous components is output from the light source, and concentrations of the gaseous components are obtained based on light intensity detected by the detector. The gas analysis device sets a cumulative measurement time for the mid-infrared lights with the wavelengths for respective ones of the measurement target gaseous components; and controls at least one of an output time of the light source and a detection time of the detector in accordance with the cumulative measurement times, thereby efficiently measuring the plurality of types of gaseous components contained in the gas (Continued)

| NO (WAVELENGTH 5.40 μm) | α SECONDS | | |
| NONANAL (WAVELENGTH 5.72 μm) | | β SECONDS | |
| ACETALDEHYDE (WAVELENGTH 5.70 μm) | | | γ SECONDS |
| ACETONE (WAVELENGTH 5.76 μm) | | | | ζ SECONDS | by using the mid-infrared lights with the plurality of wavelengths.

13 Claims, 6 Drawing Sheets

(51) Int. Cl.
 *G01N 33/497* (2006.01)
 *A61B 5/097* (2006.01)
 *A61B 5/00* (2006.01)
 *G01N 33/00* (2006.01)
 *G01N 21/03* (2006.01)

(52) U.S. Cl.
 CPC ....... *A61B 5/7278* (2013.01); *G01N 21/3504* (2013.01); *G01N 33/0036* (2013.01); *G01N 33/497* (2013.01); *G01N 21/031* (2013.01); *G01N 2033/4975* (2013.01); *G01N 2201/06113* (2013.01)

(56) References Cited

U.S. PATENT DOCUMENTS

2007/0064748 A1* 3/2007 Mirov ................... C30B 31/00
                                                              372/20
2012/0287418 A1* 11/2012 Scherer ................. G01N 21/61
                                                              356/51

OTHER PUBLICATIONS

European search report issued for counterpart European Application 14842376.7, issued by European Patent Office dated Oct. 5, 2016.
Asobe M et al: "Engineered Quasi-Phase Matching Device for Unequally Spaced Multiple Wavelength Generation and its Application to Midinfrared Gas Sensing", IEEE Journal of Quantum Electronics, IEEE Service Center, Piscataway, NJ, USA, vol. 46, No. 4, Apr. 1, 2010 (Apr. 1, 2010), pp. 447-453, XP011302845 ISSN: 0018-9197.
Chen W et al: "Midinfrared cw difference-frequency generation using a synchronous scanning technique for continuous tuning of the full spectral region from 4.7 to 6.5 mum", Review of Scientific Instruments, AIP, Melville, NY, US, vol. 67, No. 10, Oct. 1, 1996 (Oct. 1, 1996), pp. 3411-3415, XP000635800 ISSN: 0034-6748, DOI: 10.1063/1.1147151.
Wang C and Sahay P: "Breath Analysis Using Laser Spectroscopic Techniques: Breath Biomarkers, Spectral Fingerprints, and Detection Limits", Sensors, vol. 9, No. 10, Oct. 19, 2009 (Oct. 19, 2009), pp. 8230-8262, XP55023621, DOI: 10.3390/s91008230.
Marinov D et al: "Mid-infrared spectroscopic investigation of methylamines by a continuous-wave difference-frequency-generation-based system", Applied Optics, Optical Society of America, Washington, DC; US, vol. 47, No. 12, Apr. 20, 2008 (Apr. 20, 2008), pp. 1956-1962, XP002753797, ISSN: 0003-6935, DOI: 10.1364/AO.47.001956.
"Trace gas sensing and chemical reaction kinetics study by using laser spectroscopy", Koji Miyazaki, Masaki Yumoto, (RIKEN), Yoshizumi Kajii, (Kyoto University), Satoshi Wada, (RIKEN), IEE Japan (2015).

* cited by examiner

FIG. 5

| | |
|---|---|
| NO (WAVELENGTH 5.40 μm) | α SECONDS |
| NONANAL (WAVELENGTH 5.72 μm) | β SECONDS |
| ACETALDEHYDE (WAVELENGTH 5.70 μm) | γ SECONDS |
| ACETONE (WAVELENGTH 5.76 μm) | ζ SECONDS |

US 9,861,297 B2

GAS ANALYSIS DEVICE AND GAS ANALYSIS METHOD

BACKGROUND

1. Technical Field

The present invention relates to a gas analysis device and a gas analysis method that analyze a plurality of gaseous components contained in a gas.

2. Related Art

Biogenic gases such as human exhaled gases, skin gases and rectum gases (flatulence) contain several hundred sort of types of gaseous substances such as volatile organic compounds (VOCs). They include substances that have causal relationships with diseases, and such knowledge has been increasingly applied to biogenic gas diagnoses that diagnose diseases by quantitatively analyzing these substances as markers. Therefore, researches for identifying VOCs correlated with diseases, and research and development for new measurement/analysis methods have been vigorously performed.

As one of approaches to simple and rapid measurement of trace amounts of components in a biogenic gas, there is absorption spectrometry that utilizes a mid-IR laser. In order to detect a known VOCs correlated with diseases, this approach determines the component concentration by absorption spectroscopic measurement by using, as a light source, a narrow band mid-IR laser whose wavelength is caused to match the absorption spectrum of the component. For example, the quantity of nitrogen monoxide (NO) in a biogenic gas that enables distinction between asthma and chronic coughing can be determined by a quantum cascade laser with a wavelength of 5.27 μm (1898 $cm^{-1}$), and a detection lower limit of approximately 1 ppb has been realized. Also, acetaldehyde that is originated from lung cancer can be measured with a detection lower limit of 80 ppb by utilizing a quantum cascade laser of 5.79 μm (1727 $cm^{-1}$).

The VOCs correlated with diseases, and their infrared absorption spectrums are shown in FIG. 4. The characteristic absorption bands of functional groups such as aldehyde, ketone, carboxylic acid and amide that are important as biogenic products concentrate around 1600 to 1800 $cm^{-1}$, and a number of the characteristic absorption spectra unique to molecules are distributed in a region around 800 to 1400 $cm^{-1}$ which region is also called a finger-print region of molecules.

Currently, the effective wavelength tuning region of a mid-IR laser whose spectrum width is narrowed is very narrow at several $cm^{-1}$, and it has been becoming difficult to perform simultaneous measurement of a plurality of gases. To cope with this, development of an analysis device for a plurality of gaseous components contained in a gas that utilizes a light source having a narrow spectrum and a wide wavelength tuning region in the mid-IR region has been anticipated.

Patent Document 1 proposes a method in which: a multiplexed beam formed by combining a near-IR pump beam and a near-IR signal beam from a semiconductor laser for detecting a first gas medium is caused to enter PPLN crystal to generate a near-IR or mid-infrared difference frequency light for detecting a second gas medium; from the multiplexed beam formed by combining the signal beam, the difference frequency light and the pump beam that has passed a multi-pass cell enclosing a sample gas, only the signal beam and the difference frequency light are separated onto the same optical axis; then the signal beam and difference frequency light are caused to enter a MCT detector to detect them simultaneously; and concentrations of the first gas medium and the second gas medium are analyzed based on electrical signals from the MCT detector.

PRIOR ART DOCUMENTS

Patent Document

Patent Document 1: Japanese Patent Application Publication No. 2006-300760

Because the method proposed in Patent Document 1 does not take into consideration a detection lower limit that is different for each gaseous component or the like, that is, a cumulative measurement time, it is difficult to perform analysis of gases efficiently.

An object of the present invention is to provide a device and a method that measure a plurality of types of gaseous components efficiently by using mid-IR beams with different wavelengths.

SUMMARY

A gas analysis device of the present invention according to Claim 1 comprises:
 a cell that contains a measurement target gas;
 a light source that selects a mid-infrared light with any wavelength and outputs the mid-IR beam into the cell; and
 a detector that detects the mid-IR beam having transmitted through the cell, wherein
 two or more types of gaseous components contained in the gas are measurement targets, a mid-IR beam with a wavelength that is caused to match the absorption spectrum of the measurement target gaseous components is output from the light source, and concentrations of the gaseous components are obtained based on light intensity detected by the detector, and
 the gas analysis device comprises:
  a measurement time setting means that sets a cumulative measurement time for the mid-IR beams with the wavelengths for respective ones of the measurement target gaseous components; and
  a control means that controls at least one of an output time of the light source and a detection time of the detector in accordance with the cumulative measurement times.

According to the present invention according to Claim 2, in the gas analysis device according to Claim 1, the light source has: a first light source that outputs a first infrared beam; a second light source that outputs a second infrared beam with a wavelength that is different from the wavelength of the first infrared beam; and a wavelength conversion device that outputs a difference frequency between the first infrared beam and the second infrared beam.

According to the present invention according to Claim 3, in the gas analysis device according to Claim 2, the first light source is a laser that outputs a laser beam with a single wavelength, and the second light source is arrayed lasers that output laser beams with different wavelengths.

According to the present invention according to Claim 4, in the gas analysis device according to Claim 2 or 3, nonlinear optical crystal which is not ferroelectric crystal is used as the wavelength conversion device.

According to the present invention according to Claim 5, in the gas analysis device according to Claim 4, the nonlinear optical crystal is $AgGaS_2$ crystal.

According to the present invention according to Claim 6, in the gas analysis device according to any one of Claims 1 to 5, the measurement target gaseous components are two or more types among nitrogen monoxide, nonanal, acetaldehyde and acetone.

According to the present invention according to Claim 7, in the gas analysis device according to any one of Claims 1 to 5, the measurement target gaseous components are two or more types among ethane, nonanal, acetaldehyde, methylamine, methanol, acetone and methane.

According to the present invention according to Claim 8, in the gas analysis device according to any one of Claims 1 to 7, the measurement target gas is an exhaled gas.

According to the present invention according to Claim 9, in the gas analysis device according to any one of Claims 1 to 7, a biogenic gas such as an exhaled gas, a skin gas or a rectum gas is the measurement target gas, and bronchial asthma, lung cancer, pulmonary disease, renal failure, pneumonia, *Helicobacter pylori*, diabetes, obesity or gastrointestinal disorder is identified based on the concentrations of the gaseous components detected.

In a gas analysis method of the present invention according to Claim 10 that measures a concentration of gaseous components in a measurement target gas by using intensity of a light with a wavelength in a mid-infrared region that is caused to match the absorption spectrum of the gaseous components, at least a first gaseous component and a second gaseous component are the measurement target gaseous components, a mid-IR beam with a first wavelength corresponding to the first gaseous component and a mid-IR beam with a second wavelength corresponding to the second gaseous component are used, and a cumulative measurement time during which the mid-IR beam with the first wavelength is used and a cumulative measurement time during which the mid-IR beam with the second wavelength is used are made different from each other.

According to the present invention according to Claim 11, in the gas analysis method according to Claim 10, the measurement target gas is an exhaled gas.

Effects of the Invention

The present invention can realize a device and a method that measure a plurality of types of gaseous components in a measurement target gas efficiently by using mid-IR beams with a plurality of wavelengths.

BRIEF DESCRIPTION OF THE DRAWINGS

FIG. 5 shows an output time of mid-IR beams corresponding to each gaseous component of the gas analysis device.

DESCRIPTION OF EXEMPLARY EMBODIMENTS

Figure 1:
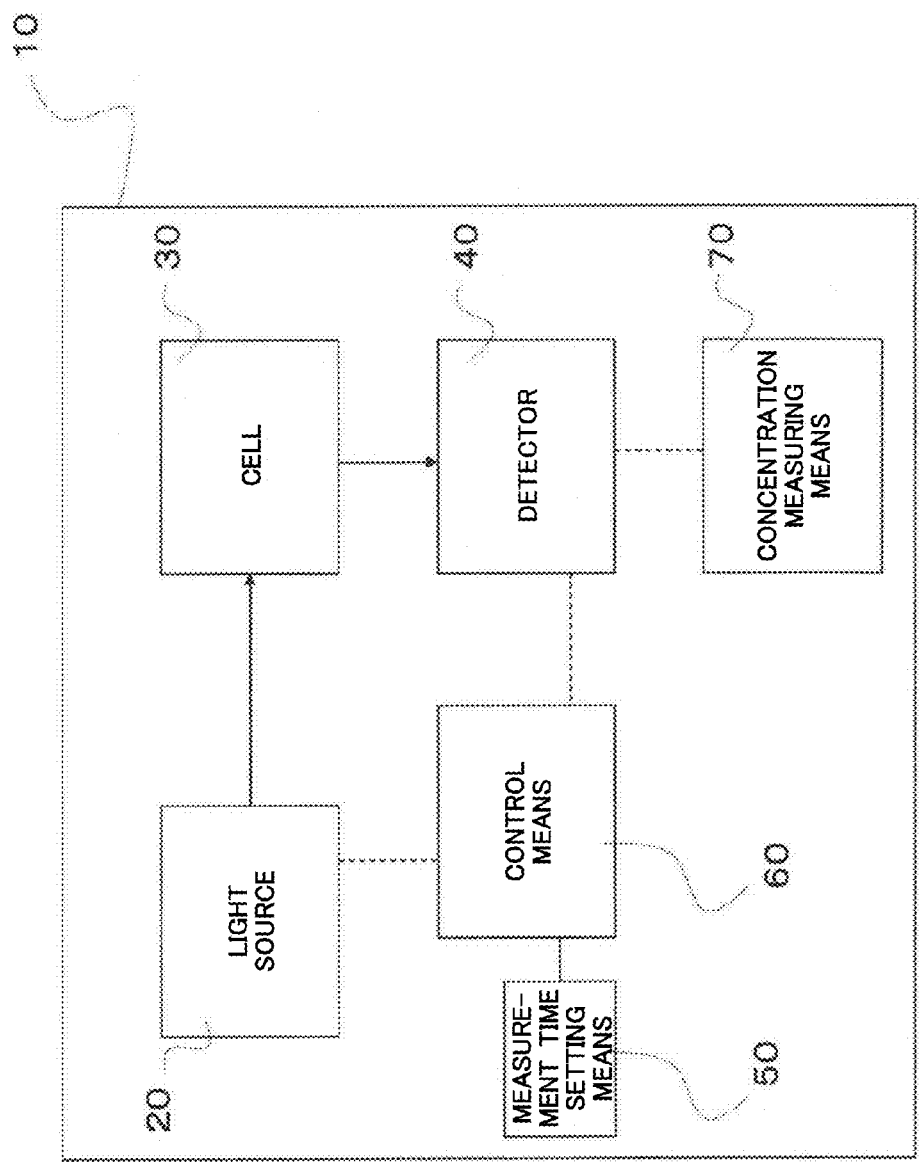
FIG. 1 illustrates the overall gist of a gas analysis device according to one example of the present invention.

A gas analysis device according to a first embodiment of the present invention has: a measurement time setting means that sets a cumulative measurement time of a mid-infrared beam with a wavelength for respective ones of measurement target gaseous components; and a control means that controls at least one of an output time of a light source and a detection time of a detector in accordance with the cumulative measurement times. According to the present embodiment, the cumulative measurement time can be set in accordance with a detection lower limit value required for pathological diagnosis being different for each gaseous component, and the cumulative measurement time can be set by taking into consideration the absorption intensity attributable to differences among absorption regions of gaseous components; therefore, the concentration measurement of each gaseous component can be performed surely.

According to a second embodiment of the present invention, in the gas analysis device according to the first embodiment, the light source consists of: a first light source that outputs a first infrared beam; a second light source that outputs a second infrared beam with a wavelength that is different from the wavelength of the first infrared beam; and a wavelength conversion device that outputs a difference frequency between the first infrared beam and the second infrared beam. According to the present embodiment, by changing the wavelengths of the first infrared beam and the second infrared beam, the wavelength of a mid-infrared beam output from the wavelength conversion device can be changed.

According to a third embodiment of the present invention, in the gas analysis device according to the second embodiment, the first light source is a laser that outputs a laser beam with a single wavelength, and the second light source is arrayed lasers that output laser beams with different wavelengths. According to the present embodiment, by changing the wavelength of an infrared beam output from the second light source without changing the wavelength of an infrared beam output from the first light source, the wavelength of a mid-infrared beam output from the wavelength conversion device can be changed. Furthermore, by employing an arrayed laser for the second light source, the wavelength of an infrared beam can be changed only by switching internal elements.

According to a fourth embodiment of the present invention, in the gas analysis device according to the second or third embodiment, nonlinear optical crystal which is not ferroelectric crystal is used as the wavelength conversion device. According to the present embodiment, it becomes possible to output a mid-infrared beam having the light transmission region up to a long wavelength of 5 μm or longer.

According to a fifth embodiment of the present invention, in the gas analysis device according to the fourth embodiment, the nonlinear optical crystal is $AgGaS_2$ crystal. According to the present embodiment, because among nonlinear optical crystal which is not ferroelectric crystal, high quality $AgGaS_2$ crystal can be obtained, improvement of quality can be attempted.

According to a sixth embodiment of the present invention, in the gas analysis device according to any one of the first to fifth embodiments, the measurement target gaseous components are two or more types among nitrogen monoxide, nonanal, acetaldehyde and acetone. According to the present embodiment, the concentrations of these gaseous components can be measured at the infrared absorption region of approximately 1600 to 1800 $cm^{-1}$.

According to a seventh embodiment of the present invention, in the gas analysis device according to any one of the first to fifth embodiments, the measurement target gaseous components are two or more types among ethane, nonanal, acetaldehyde, methylamine, methanol, acetone and methane. According to the present embodiment, the concentrations of these gaseous components can be measured at the infrared absorption region of approximately 2800 to 3000 $cm^{-1}$.

According to an eighth embodiment of the present invention, in the gas analysis device according to any one of the first to seventh embodiment, a measurement target gas is an exhaled gas. According to the present embodiment, an exhaled gas analysis device that measures a plurality of gaseous components contained in an exhaled gas can be configured.

According to a ninth embodiment of the present invention, in the gas analysis device according to any one of the first to seventh embodiments, a biogenic gas such as an exhaled gas, a skin gas or a rectum gas is a measurement target gas, and bronchial asthma, lung cancer, pulmonary disease, renal failure, pneumonia, *Helicobacter pylori*, diabetes, obesity or gastrointestinal disorder is identified based on the concentrations of the gaseous components detected. According to the present embodiment, because gaseous components that enable identification of the pathology of these diseases have their characteristic absorption bands in the mid-infrared absorption region, the pathology of the diseases can be identified.

In a gas analysis method according to a tenth embodiment of the present invention, at least a first gaseous component and a second gaseous component are measurement target gaseous components, a mid-infrared beam with a first wavelength corresponding to the first gaseous component and a mid-infrared beam with a second wavelength corresponding to the second gaseous component are used, and a cumulative measurement time during which the mid-infrared beam with the first wavelength is used and a cumulative measurement time during which the mid-infrared beam with the second wavelength is used are made different from each other. According to the present embodiment, the cumulative measurement time can be set in accordance with a detection lower limit value required for pathological diagnosis being different, and the cumulative measurement time can be set by taking into consideration the absorption intensity attributable to differences among absorption regions of gaseous components; therefore, the concentration measurement of each gaseous component can be performed surely.

According to an eleventh embodiment of the present invention, in the gas analysis method according to the tenth embodiment, a measurement target gas is an exhaled gas. According to the present embodiment, a plurality of gaseous components contained in an exhaled gas can be measured.

Examples

Hereinafter, a gas analysis device according to one example of the present invention is explained by using figures. It should be noted that in the present example, an exhaled gas analysis device that uses an exhaled gas as a biogenic gas is explained as a gas analysis device.

FIG. 1 illustrates the overall gist of the gas analysis device.

A gas analysis device 10 comprises: a light source 20 that selects a mid-infrared beam with any wavelength and outputs the mid-infrared beam; a cell 30 that contains an exhaled gas of an analysis target and receives the mid-infrared beam from the light source 20; a detector 40 that detects the mid-infrared beam having transmitted through the cell 30; a measurement time setting means 50 that sets a cumulative measurement time for the mid-infrared beam; a control means 60 that controls one of an output time of the light source 20 and a detection time of the detector 40 in accordance with the cumulative measurement time; and a concentration measuring means 70 that obtains the concentration of a gaseous component based on light intensity detected by the detector 40. It should be noted that the control means 60 may control both the output time of the light source 20 and the detection time of the detector 40 in accordance with the cumulative measurement time.

At the light source 20, a mid-infrared beam with a wavelength corresponding to the absorption spectrum of a measurement target gaseous component is output. At the measurement time setting means 50, a cumulative measurement time of mid-infrared lights with wavelengths corresponding to respective measurement target gaseous components is set. At the control means 60, according to the set cumulative measurement time, at least one of an output time of a mid-infrared beam output from the light source 20 and a detection time of the detector 40 is made different for each wavelength.

At the gas analysis device 10, two or more types of gaseous components in an exhaled gas contained in the cell 30 are measurement targets, mid-infrared beams with wavelengths that are caused to match the absorption spectra of measurement target gaseous components are output from the light source 20 into the cell 30, and the concentrations of the gaseous components are obtained at the concentration measuring means 70 based on light intensity detected by the detector 40.

Figure 2:
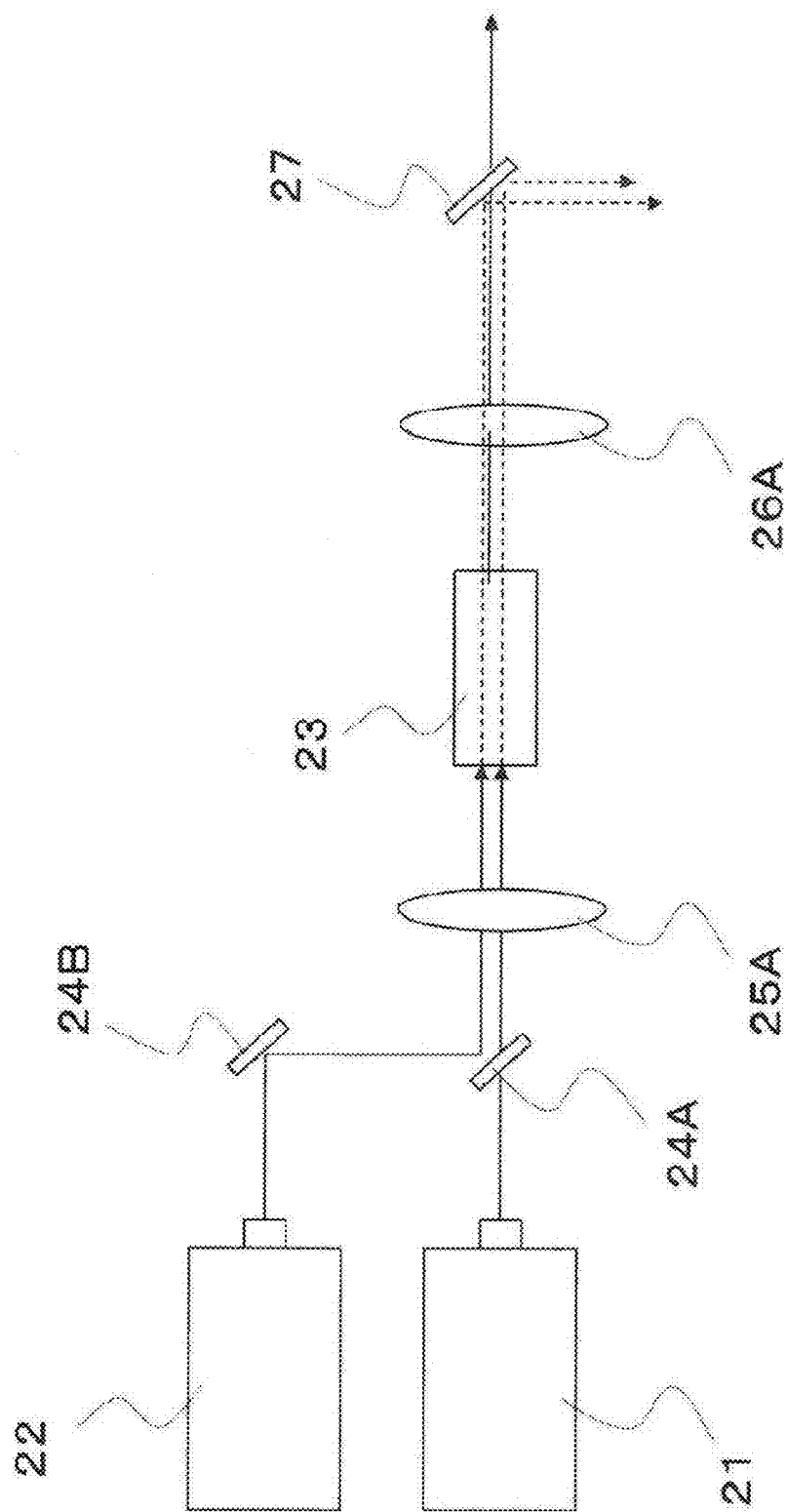
FIG. 2 illustrates the configuration of a light source of the gas analysis device.

FIG. 2 illustrates the configuration of the light source of the gas analysis device according to the present example.

The light source 20 according to the present example has: a first laser as a first light source 21 that outputs a first laser beam; a second laser as a second light source 22 that outputs a second laser beam with a wavelength different from the wavelength of the first laser beam; and a wavelength conversion device 23. The first laser beam enters the wavelength conversion device 23 via a mirror 24A and a lens 25A, and the second laser beam enters the wavelength conversion device 23 via a mirror 24B and the lens 25A. The two laser beams that have entered the wavelength conversion device 23 are converted into a beam that corresponds to the difference between their frequencies (difference frequency), and the mid-infrared beam generated by the conversion is output to the cell 30 via a lens 26A and a filter 27.

Here, continuous wave oscillating (CW operation)-type distribution feedback semiconductor lasers (DFB lasers) are used for the first light source (first laser) 21 and the second light source (second laser) 22. As DFB lasers, light sources that have a narrow spectrum in the near-infrared region of approximately 1 μm to 1.7 μm, and allow free selection of oscillating wavelengths have been developed. Furthermore, by configuring the light source 20 by using a small-sized laser diode, the gas analysis device 10 is allowed to have a small size so that the gas analysis device 10 can be configured as a portable one, and it becomes possible to use it by carrying it to various locations.

It should be noted that pulse-operation type distribution feedback semiconductor lasers (DFB lasers) may be used for the first light source (first laser) 21 and the second light source (second laser) 22. Because by using pulse-operation type DFB lasers, the efficiency of wavelength conversion can be improved due to their high peak power, and accordingly, the power of a mid-infrared light to be obtained becomes high, measurement at a high S/N ratio (signal/noise ratio) becomes possible. Also, when pulse operation is employed, detecting elements of an MCT detector 41 described below can be formed into one element by utilizing time differences of each pulse.

Also, AgGaS$_2$ crystal is used for the wavelength conversion device 23. AgGaS$_2$ crystal can be excited by a DFB laser, and has a light transmission region for a long wavelength longer than 5 μm (about 13 μm) while ferroelectric crystal such as LiNbO$_3$ crystal is opaque for a mid-infrared region of 5 μm (2000 cm$^{-1}$) or longer.

The first laser 21 is a laser that outputs a single wavelength, and in the present example, outputs a laser with a wavelength of 1064 nm. The second laser 22 is arrayed, and is a wavelength tuning laser that is able to output lasers with a plurality of wavelengths. Accordingly, by switching elements inside the second laser 22 by signals from the control unit 60, it is possible to change the wavelength of the second laser output from the second laser 22, and to output, from the wavelength conversion device 23, mid-infrared beams with different wavelengths (converted lights). In the present example, the second laser 22 has, within itself, four elements so that laser beams with wavelengths of 1325 nm, 1307 nm, 1308 nm and 1305 nm can be output.

It should be noted that the light source 20 may not utilize generation of difference frequencies as in the present example, but for example, may be configured by using a quantum cascade laser, and may be configured by using a plurality of or a single infrared laser diode (infrared LD).

Figure 3:
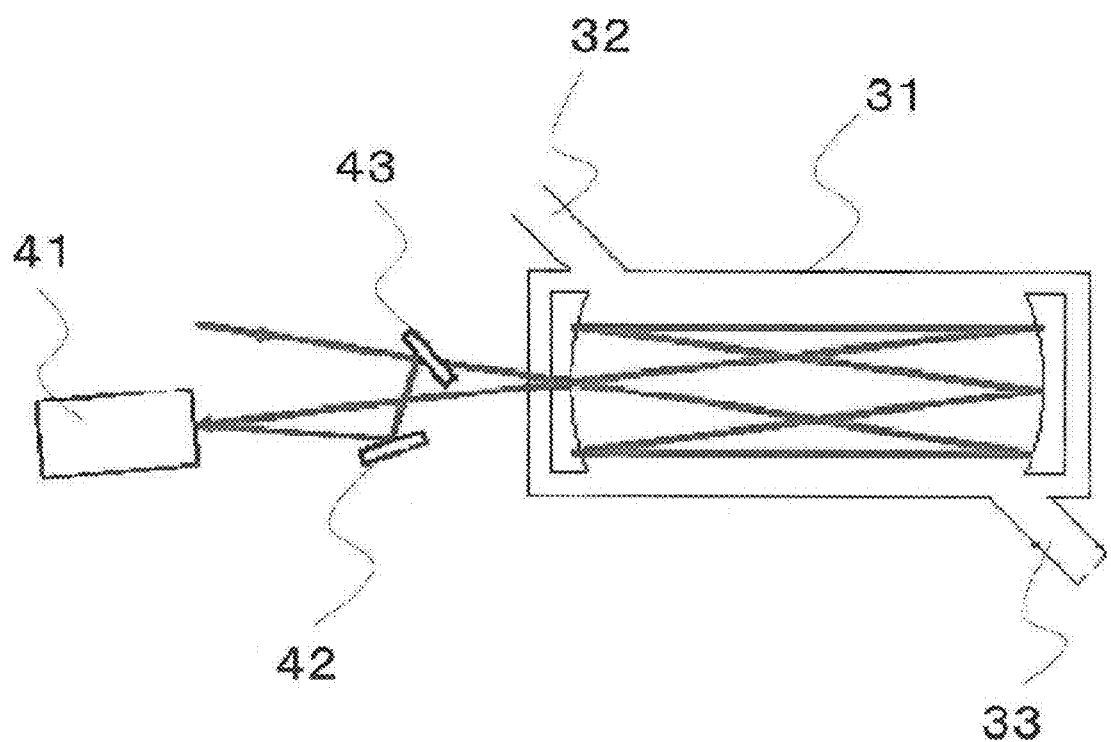
FIG. 3 illustrates the configuration of a cell and a detector of the gas analysis device.

FIG. 3 illustrates the configuration of the cell and detector of the gas analysis device according to the present example.

A multi-pass cell 31 is used for the cell 30 according to the present example. The multi-pass cell 31 comprises an inlet port 33 for introducing an exhaled gas into the multi-pass cell 31, and an exhaust port 32 for discharging the exhaled gas from the multi-pass cell 31.

Here, an astigmatism Herriot multi-pass cell that can ensure a long optical path length relative to a cell capacity is preferably used for the multi-pass cell 31. By employing an astigmatism Herriot multi-pass cell, a long optical path length (about 210 m) can be attained, and a sampling amount of an exhaled gas can be reduced. However, the multi-pass cell 31 is not limited to a Herriot multi-pass cell, but the multi-pass cell 31 employing another system may be used.

Also, the detector 40 according to the present example consists of: the MCT detector 41 that is sensitive to the mid-infrared region; a mirror 42; and a beam splitter 43, and a mid-infrared light output from the wavelength conversion device 23 is split by the beam splitter 43, one mid-infrared light enters the MCT detector 41 through the multi-pass cell 31, and the other mid-infrared light enters the MCT detector 41 via the mirror 42.

It should be noted that the detector 40 may be configured to measure only a specific wavelength by being provided with a wavelength selective filter.

Next, a case where targets of simultaneous measurement are nitrogen monoxide (NO), nonanal, acetaldehyde and acetone among gaseous components contained in an exhaled gas is explained as an example.

Figure 4:
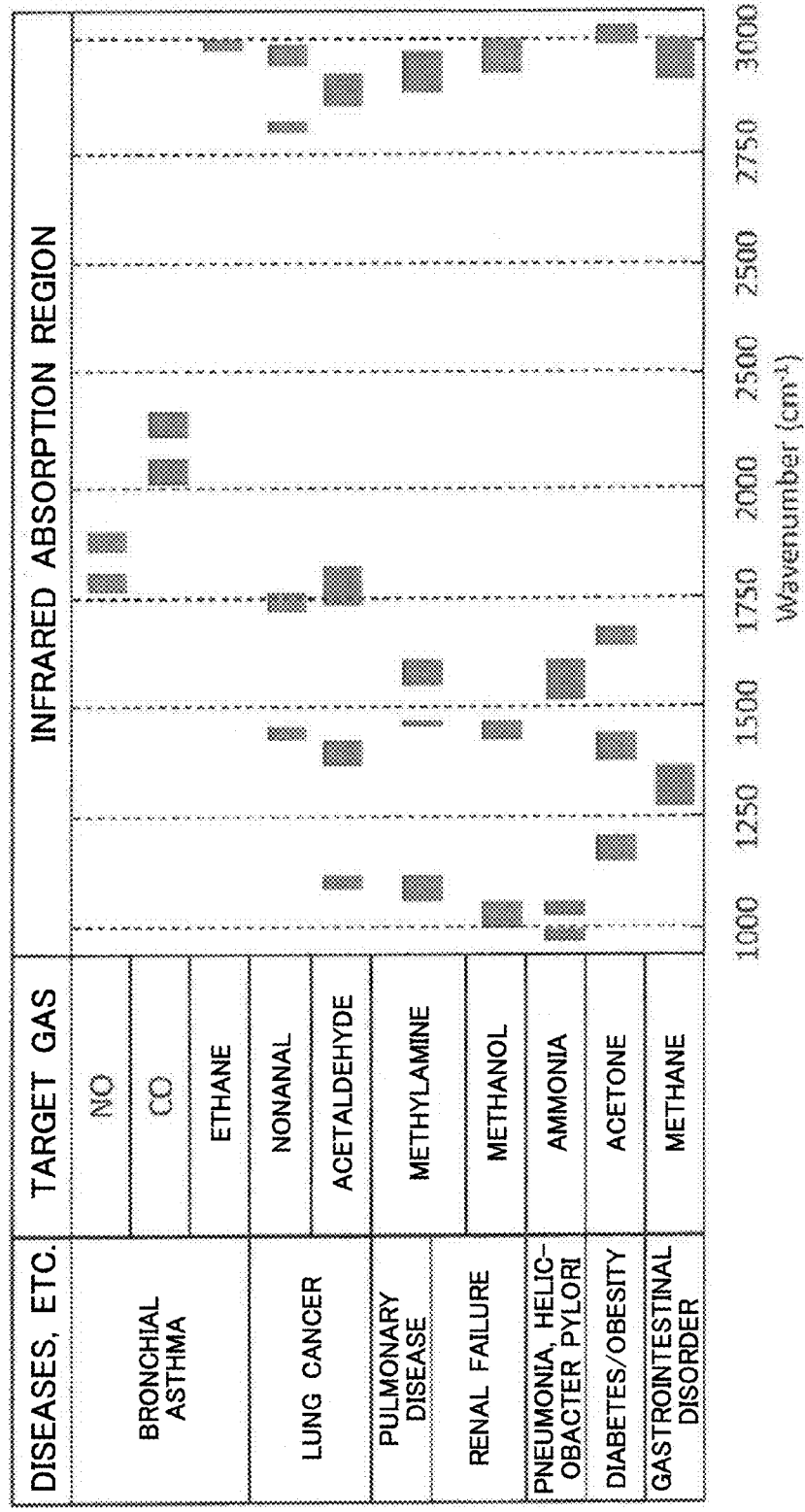
FIG. 4 shows the VOCs correlated with diseases, and their infrared absorption spectrums.

As shown in FIG. 4, the infrared absorption regions of the above-mentioned four gaseous components are distributed around 1600 cm$^{-1}$ to 1800 cm$^{-1}$. For example, the concentration of each component can be measured by utilizing a mid-infrared beam of 5.40 μm (1852 cm$^{-1}$) for nitrogen monoxide (NO), a mid-infrared beam of 5.72 μm (1748 cm$^{-1}$) for nonanal, a mid-infrared light of 5.70 μm (1754 cm$^{-1}$) for acetaldehyde, and a mid-infrared beam of 5.76 μm (1736 cm$^{-1}$) for acetone.

Before starting measurement, the inlet port 33 of the multi-pass cell 31 is opened in a state where the exhaust port 32 is opened, and after introducing an exhaled gas to be measured into the multi-pass cell 31, the exhaust port 32 and the inlet port 33 are closed.

Also, FIG. 5 shows an output time of a mid-infrared beam corresponding to each gaseous component of the gas analysis device according to the present example, and with the measurement time setting means 50, the output time may be set at α seconds for nitrogen monoxide (NO), β seconds for nonanal, γ seconds for acetaldehyde, and ζ seconds for acetone.

When measurement is started, first in order to measure the concentration of nitrogen monoxide (NO), based on an instruction from the control unit 60, the angle of AgGaS$_2$ crystal of the wavelength conversion device 23 is adjusted to about 48.9 deg., and the first laser beam with a wavelength of 1064 nm and the second laser beam with a wavelength of 1325 nm are output from the first laser 21 and the second laser 22, respectively. As a result, a converted mid-infrared beam with a wavelength of 5.40 μm (1852 cm$^{-1}$) is generated at the wavelength conversion device 23. The generated mid-infrared beam with a wavelength of 5.40 μm is split by the beam splitter 43, one mid-infrared beam enters the MCT detector 41 through the multi-pass cell 31 into which the exhaled gas has been introduced, and the other mid-infrared beam enters the MCT detector 41 via the mirror 42. Then, the concentration of nitrogen monoxide (NO) is obtained at the concentration measuring means 70 based on light intensity detected by the MCT detector 41.

When the duration of measurement reaches the cumulative measurement time α seconds set for nitrogen monoxide (NO), next in order to measure the concentration of nonanal, based on an instruction from the control unit 60, the light source 20 changes the angle of AgGaS$_2$ crystal of the wavelength conversion device 23 to about 47.4 deg., and switches the wavelength of the laser output from the second laser 22 to 1307 nm. As a result, a converted mid-infrared beam with a wavelength of 5.72 μm (1748 cm$^{-1}$) is generated at the wavelength conversion device 23. The generated mid-infrared beam with a wavelength of 5.72 μm is split by the beam splitter 43, one mid-infrared beam enters the MCT detector 41 through the multi-pass cell 31 into which an exhaled gas has been introduced, and the other mid-infrared beam enters the MCT detector 41 via the mirror 42. Then, the concentration of nonanal is obtained at the concentration measuring means 70 based on light intensity detected by the MCT detector 41.

When the duration of measurement reaches the cumulative measurement time β seconds set for nonanal, next in order to measure the concentration of acetaldehyde, based on an instruction from the control unit 60, the light source 20 changes the angle of AgGaS$_2$ crystal of the wavelength conversion device 23 to about 47.5 deg., and switches the wavelength of the laser output from the second laser 22 to 1308 nm. As a result, a converted mid-infrared beam with a wavelength of 5.70 μm (1754 cm$^{-1}$) is generated at the wavelength conversion device 23. The generated mid-infrared beam with a wavelength of 5.70 μm is split by the beam splitter 43, one mid-infrared beam enters the MCT detector 41 through the multi-pass cell 31 into which an exhaled gas has been introduced, and the other mid-infrared beam enters the MCT detector 41 via the mirror 42. Then, the concentration of acetaldehyde is obtained at the concentration measuring means 70 based on light intensity detected by the MCT detector 41.

When the duration of measurement reaches the cumulative measurement time γ seconds set for acetaldehyde, next in order to measure the concentration of acetone, based on an instruction from the control unit 60, the light source 20 changes the angle of $AgGaS_2$ crystal of the wavelength conversion device 23 to about 47.3 deg., and switches the wavelength of the laser output from the second laser 22 to 1305 nm. As a result, a converted mid-infrared beam with a wavelength of 5.76 μm (1736 $cm^{-1}$) is generated at the wavelength conversion device 23. The generated mid-infrared beam with a wavelength of 5.76 μm is split by the beam splitter 43, one mid-infrared beam enters the MCT detector 41 through the multi-pass cell 31 into which an exhaled gas has been introduced, and the other mid-infrared beam enters the MCT detector 41 via the mirror 42. Then, the concentration of acetone is obtained at the concentration measuring means 70 based on light intensity detected by the MCT detector 41. When the duration of measurement reaches the cumulative measurement time of ζ seconds set for acetone, the light source 20 stops output of infrared lights from the first laser 21 and the second laser 22 based on an instruction from the control unit 60.

After finishing measurement of all the measurement target gaseous components in the above-mentioned manner, the exhaust port 32 is opened to discharge the exhaled gas introduced into the multi-pass cell 31.

It should be noted that the control means 60 may perform control such that a time period during which the detector 40 does not detect a mid-infrared beam is provided after starting or finishing measurement of each gaseous component, e.g., after switching from measurement of nitrogen monoxide (NO) to measurement of nonanal or before switching from measurement of acetaldehyde to measurement of acetone.

Although in the above-mentioned example, the output time of a mid-infrared beam is made different for each gaseous component as in FIG. 5, the output time of a mid-infrared beam may remain the same even when a measurement target gaseous component changes, and for example, the cumulative measurement time may be adjusted by changing detection time at the detector 40 by controlling, with a shutter, a time during which the mid-infrared beam enters the detector 40.

Also, although in the above-mentioned example, a case where targets of simultaneous measurement are nitrogen monoxide (NO), nonanal, acetaldehyde and acetone was explained, targets of simultaneous measurement may be two or more types among ethane, nonanal, acetaldehyde, methylamine, methanol, acetone and methane ($CH_4$). As shown in FIG. 4, the infrared absorption regions of these gaseous components are distributed around 2800 $cm^{-1}$ to 3000 $cm^{-1}$, and by utilizing a mid-infrared beam with a wavelength in this range, the concentration of each component can be measured.

Figure 6:
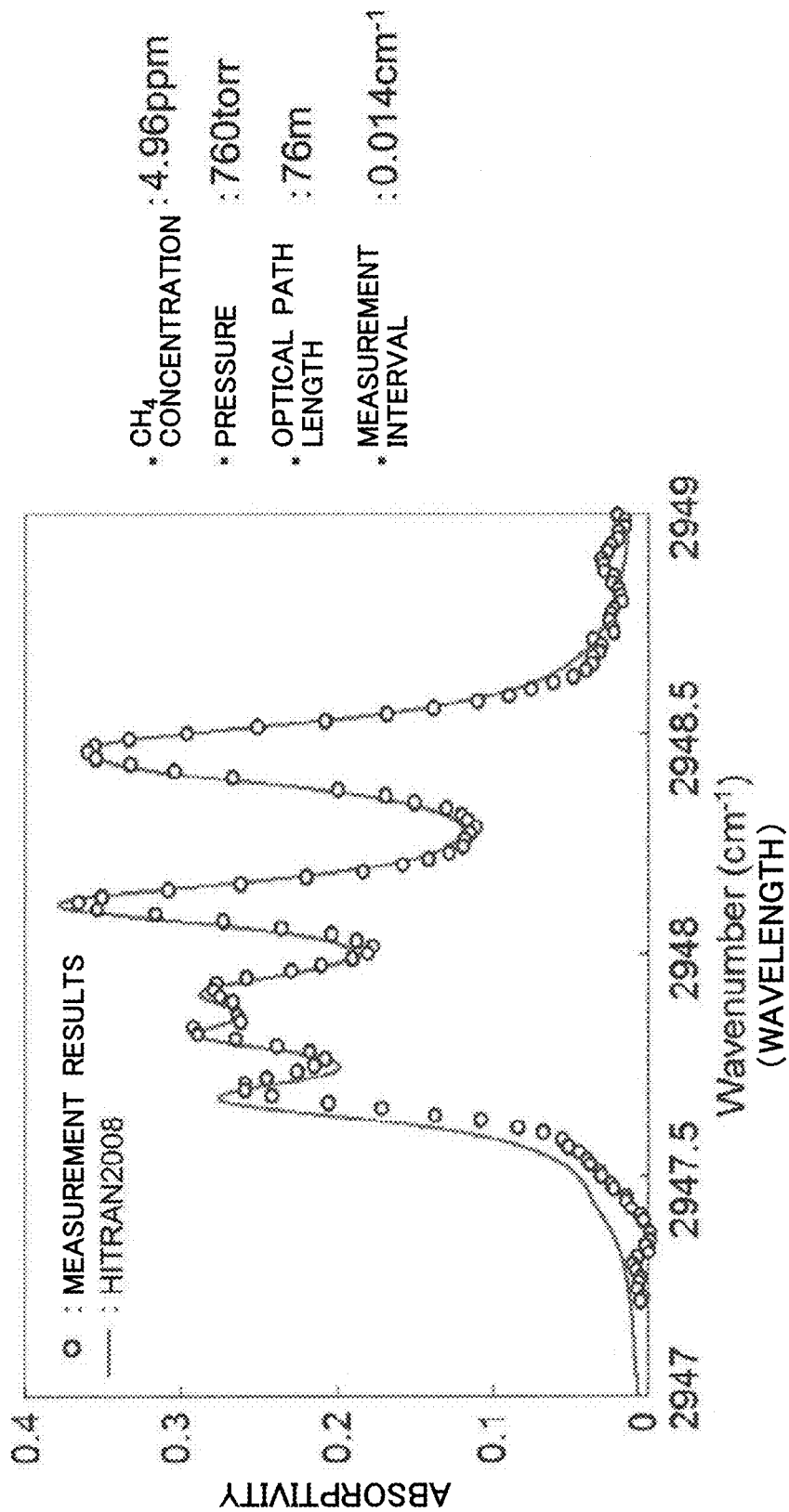
FIG. 6 shows results of measurement of methane ($CH_4$) by using the gas analysis device.

It should be noted that FIG. 6 shows results of measurement of methane ($CH_4$) by using the gas analysis device according to the present example. The concentration of methane ($CH_4$) was 4.96 ppm, the pressure within the multi-pass cell 31 was 760 Torr, the optical path length of the multi-pass cell 31 was 76 m, and the measurement intervals were 0.014 $cm^{-1}$.

White circles (○) indicate the measurement results, the solid line indicates the absorption spectrum calculated based on the HITRAN 2008 database, and it can be known that both the data approximately match each other around the wavelength 3.39 μm (2948 $cm^{-1}$).

According to the above-mentioned example, at least a first gaseous component and a second gaseous component are measurement target gaseous components, a first wavelength corresponding to a first gaseous component and a second wavelength corresponding to a second gaseous component are used, and a cumulative measurement time during which first wavelength is used and a cumulative measurement time during which second wavelength is used are made different from each other. Thereby, the cumulative measurement time can be set in accordance with a detection lower limit value required for pathological diagnosis being different, and the cumulative measurement time can be set by taking into consideration the absorption intensity attributable to differences among absorption regions of gaseous components; therefore, the concentration measurement of each gaseous component can be performed surely.

Also, according to the above-mentioned example, because gaseous components that enable identification of the pathology of bronchial asthma, lung cancer, pulmonary disease, renal failure, pneumonia, *Helicobacter pylori*, diabetes, obesity or gastrointestinal disorder have their characteristic absorption bands in the mid-infrared absorption region, the pathology of these diseases can be identified.

It should be noted that although the exhaled gas analysis device that uses an exhaled gas as a biogenic gas is explained as the gas analysis device in the above-mentioned example, the present invention can be utilized for a gas analysis device that uses biogenic gases such as skin gases, rectum gases (flatulence), gases that are expelled through affected parts treated in surgical operations or other gases, and diagnoses of diseases, drugs, doping, virus infection or the like can be performed.

Also, the present invention can be utilized in fields other than the medical field. The following are some of the examples: in agriculture, the present invention can be utilized as an agricultural product gas analysis device that uses gases expelled from plants, in diagnosing diseases, grasping growth states, identifying the place where an agricultural product was produced, or determining whether agricultural chemicals have been used; in animal husbandry, the present invention can be utilized as an animal gas analysis device that uses gases originated from animals in diagnosing diseases; in food control, the present invention can be utilized as a food gas analysis device that uses gases originated from foods in determining the place where a food was produced or grasping the fermentation and ripeness state of a fermented food; in disaster relief, the present invention can be utilized as a victim exhaled gas analysis device that uses exhaled gases of victims as markers in discovering survivors buried in rubble or the like; in indoor environment monitoring, the present invention can be utilized as an indoor floating gas analysis device in detecting allergens; and in environmental conservation, the present invention can be utilized as an atmosphere floating gas analysis device in monitoring exhaust gases from automobiles and factories.

INDUSTRIAL APPLICABILITY

The present invention can be utilized for a device and a method that measure a plurality of types of gaseous components in a measurement target gas efficiently by using mid-infrared lights with a plurality of wavelengths. Also, by monitoring gaseous components in a biogenic gas by using a device or a method according to the present invention, development as healthcare for diagnosing the health state of a human is possible, and preventive medicine and reduction of medical costs become possible.

EXPLANATION OF REFERENCE SYMBOLS

10: gas analysis device
20: light source
21: first light source (first laser)
22: second light source (second laser)
23: wavelength conversion device
24A: mirror
24B: mirror
25A: lens
26A: lens
27: filter
30: cell
31: multi-pass cell
32: exhaust port
33: inlet port
40: detector
41: MCT detector
42: mirror
43: beam splitter
50: measurement time setting means
60: control means
70: concentration measuring means

What is claimed is:

1. A gas analysis device comprising:
a cell that contains a measurement target gas;
a light source that selects a mid-infrared light with any wavelength and outputs the mid-infrared light into the cell; and
a detector that detects the mid-infrared light having transmitted through the cell, wherein two or more types of gaseous components contained in the gas are measurement targets, a mid-infrared light with a wavelength that is caused to match the absorption spectrum of the measurement target gaseous components is output from the light source, and concentrations of the gaseous components are obtained based on light intensity detected by the detector;
a measurement time setting means that sets a cumulative measurement time for the mid-infrared lights, the cumulative measurement time being made different for each wavelength for respective measurement target gaseous components; and
a control means that controls at least one of an output time of the light source and a detection time of the detector in accordance with the cumulative measurement times.

2. The gas analysis device according to claim 1, wherein the light source has: a first light source that outputs a first infrared beam; a second light source that outputs a second infrared beam with a wavelength that is different from the wavelength of the first infrared beam; and a wavelength conversion device that outputs a difference frequency between the first infrared beam and the second infrared beam.

3. The gas analysis device according to claim 2, wherein the first light source is a laser that outputs a laser beam with a single wavelength, and the second light source is arrayed lasers that output laser beams with different wavelengths.

4. The gas analysis device according to claim 2, wherein nonlinear optical crystal which is not ferroelectric crystal is used as the wavelength conversion device.

5. The gas analysis device according to claim 4, wherein the nonlinear optical crystal is $AgGaS_2$ crystal.

6. The gas analysis device according to claim 1, wherein the measurement target gaseous components are two or more types among nitrogen monoxide, nonanal, acetaldehyde and acetone.

7. The gas analysis device according to claim 1, wherein the measurement target gaseous components are two or more types among ethane, nonanal, acetaldehyde, methylamine, methanol, acetone and methane.

8. The gas analysis device according to claim 1, wherein the measurement target gas is an exhaled gas.

9. The gas analysis device according to claim 1, wherein a biogenic gas such as an exhaled gas, a skin gas or a rectum gas is the measurement target gas, and bronchial asthma, lung cancer, pulmonary disease, renal failure, pneumonia, *Helicobacter pylori*, diabetes, obesity or gastrointestinal disorder is identified based on the concentrations of the gaseous components detected.

10. The gas analysis device according to claim 1, wherein the cell is a multi-pass cell.

11. A gas analysis method that measures a concentration of gaseous components in a measurement target gas by using intensity of a light with a wavelength in a mid-infrared region that is caused to match the absorption spectrum of the gaseous components, wherein
at least a first gaseous component and a second gaseous component are the measurement target gaseous components,
a mid-infrared light with a first wavelength corresponding to the first gaseous component and a mid-infrared light with a second wavelength corresponding to the second gaseous component are used, and
a cumulative measurement time during which the mid-infrared light with the first wavelength is used and a cumulative measurement time during which the mid-infrared light with the second wavelength is used are made different from each other.

12. The gas analysis method according to claim 11, wherein the measurement target gas is an exhaled gas.

13. The gas analysis method according to claim 11, wherein at least the first gaseous component and the second gaseous component are contained in a single cell that is a multi-pass cell.

* * * * *